United States Patent [19]

Langhals et al.

[11] Patent Number: 5,354,869
[45] Date of Patent: Oct. 11, 1994

[54] 3,6-BIS-(2'-METHOXYPHENYL)-2,5-DIHYDRO-2,5-DIMETHYL-PYRROLO-(3,4-C)-PYRROLE-1,4-DIONE COMPOUND

[75] Inventors: Heinz Langhals, Ottobrunn; Thomas Potrawa, Seelze, both of Fed. Rep. of Germany

[73] Assignee: Riedel-De Haen Aktiengesellschaft, Seelze, Fed. Rep. of Germany

[21] Appl. No.: 640,367

[22] Filed: Jan. 29, 1991

[30] Foreign Application Priority Data

Jul. 29, 1988 [DE] Fed. Rep. of Germany ....... 3825943
Jan. 24, 1989 [DE] Fed. Rep. of Germany ....... 3901988
Mar. 14, 1989 [DE] Fed. Rep. of Germany ....... 3908312

[51] Int. Cl.$^5$ ............................................. C07D 487/02
[52] U.S. Cl. ................................................... 548/453
[58] Field of Search ......................................... 548/453

[56] References Cited

FOREIGN PATENT DOCUMENTS 187620 7/1986 European Pat. Off. .

OTHER PUBLICATIONS

CA 105:153051d 1986 Chem. Abs. Service (abstract of "L" above).
CA 102:186667a 1985 Chem. Abs. Service.
CA 107:39663w (Closs) 1987 Chem Abs Ser. (abstract of Angew. Chem. 1987, 99(6) 564–7).
Potrawa et al, "Fluorescent Dyes . . .", Chem. Ber. 120, 1075–1078, 1987.

*Primary Examiner*—Marianne M. Cintins
*Assistant Examiner*—Catherine Scalzo
*Attorney, Agent, or Firm*—Connolly and Hutz

[57] ABSTRACT

A compound that is 3,6-Bis-(2'-methoxyphenyl)-2,5-dihydro-2, 5-dimethyl-pyrrolo-(3,4-c)-pyrrole-1,4-dione for the formula III

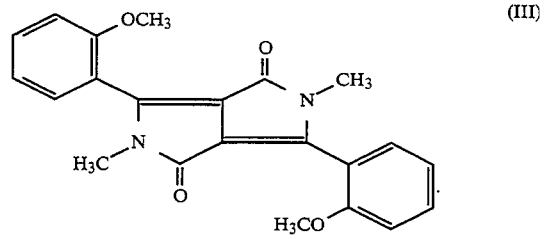

1 Claim, 1 Drawing Sheet Fig.1A.                Fig.1B.

3,6-BIS-(2'-METHOXYPHENYL)-2,5-DIHYDRO-2,5-DIMETHYL-PYRROLO-(3,4-C)-PYRROLE-1,4-DIONE COMPOUND

The present invention relates to the use of substances, in particular dyes, having at least two differently colored forms as storage media in optical memories. The invention furthermore relates to optical memories which as the storage media contains a substance, in particular a dye, having at least two differently colored forms, and to a process for loading, reading and erasing these memories and to particularly suitable dyes for use in optical memories and to processes for the preparation of these dyes.

In data processing, for example in computer systems, but also in other fields, such as, for example, in the audio and video field, memories are needed for the storage and processing of data or signals. Magnetic storage systems have predominantly been used to date for this. With these, however, an increase in the storage density can only be achieved with difficulty. Additionally, they are sensitive to magnetic fields and the long-term stability of the stored data is problematical.

Optical memories, such as, for example, CD disks, are already known for the storage of audio signals, in which the signal is read using a laser beam. Systems of this type have an excellent long-term stability. Once input, the data or signals can be read many times.

In these systems, to achieve a high information density, a boundary surface or a boundary layer, for example a metal layer, is scanned with a laser beam and input changes to the boundary surface are recorded as changes in the reflection or the transmission of the laser beam. The information is in this case recorded either thermally, such as, for example, by melting the boundary layer, or photochemically, i.e., for example, by dye bleaching processes.

However, these systems have the disadvantage that they cannot be recorded by the user and also cannot be erased. Erasable optical memories have also been developed on a magneto-optical basis or based on the phase transformation of alloys. However, optical memories of this type again have the disadvantage of a deficient long-term stability. In some cases, expensive devices are additionally required for the reading and writing process.

It has now been found that the production of easily recordable and preferably also erasable optical memories having excellent long-term stability is possible if a substance, in particular a solid substance and preferably a dye, having at least two, preferably two, differently colored forms is used as a storage medium, one form of which can be transformed by supplying energy, for example thermal energy, light energy or ultrasonic energy, into another coloured form. With two differently coloured forms, one form can be colourless and the other form can be coloured, or both forms can be differently coloured. Corresponding requirements are found, for example, in solid substances, in particular dyes, having at least two, preferably two, differently coloured allotropic forms. Each of the two differently coloured forms can then be allocated a different state of information storage (logical 0 or 1). When reading in the information, one form is transformed into the other form and consequently at the same time one logical state into the other by supplying energy, preferably thermal and/or light energy. After this transformation, the stored information can be read from optically. Normally, the state of information storage logical 0 is allocated the thermodynamically stable or more stable form of the substance or of the dye and the state of information storage logical 1 the thermodynamically metastable form of the substance or of the dye. In the case of the solid substances and dyes preferably used, the information is in this case stored in the crystal lattice of the substance or of the dye. In order that the stored information remains stable over a long period, those substances or dyes are preferred in which the transformation of the metastable form into the stable form requires the overcoming of a sufficiently large energy barrier.

For the realisation of optical memories using substances or dyes of this type which exist in two differently coloured, in particular solid and preferably crystalline, forms, an optical quality must be present in all parts of the visible route during the reading process. Precautions must also be taken in order that no problems occur as a result of scattered light. It is therefore expedient to use substances, in particular dyes, having at least one fluorescent form. In this condition, the following cases are possible for the reading in of the information: 1. Transformation of a non-fluorescent form into a fluorescent form, 2. Transformation of a fluorescent form into a non-fluorescent form and 3. Transformation of a fluorescent form into another form which is fluorescent in another region of the spectrum.

For the optical retrieval of the stored information, the above cases 1 and 2 are equivalent. For the abovementioned 3rd case, the filtering out of one of the two regions of the spectrum of the fluorescent light is necessary for reading out.

Suitable substances to be used according to the invention, in particular dyes and preferably fluorescent dyes, are known and are found, in particular, in the series comprising the 1,4-diketopyrrolopyrroles of the general formula I in which $R^1$, $R^2$, $R^3$ and $R^4$ denote hydrogen, aromatic radicals, heteroaromatic radicals, heterocyclic radicals or other non-water-solubilising radicals, and in the series comprising the perylene(dicarboximide)s of the general formula II (II)

in which $R^{11}$ and $R^{12}$ denote aromatic radicals, heteroaromatic radicals, heterocyclic radicals or other non-water-solubilising radicals.

The aromatic radicals $R^1$, $R^2$, and $R^3$ and/or $R^4$ are in particular mono- to tetracyclic and preferably mono- or bicyclic. Examples of radicals of this type are: phenyl, naphthyl, di-phenyl, phenanthryl, fluorenyl, acenaphthyl, pyrenyl, chrysenyl and naphthacenyl.

The heterocyclic aromatic radicals $R^1$, $R^2$, $R^3$ and/or $R^4$ can be purely heterocyclic or contain a heterocyclic ring and or more fused benzene rings.

The heterocyclic radicals $R^1$, $R^2$, $R^3$ and/or $R^4$ can be saturated or unsaturated and contain one or more keto, hydroxyl, sulfonyl or sulfone groups. They can contain one or more heteroatoms, in particular from the series comprising O, S and N. Suitable heterocyclic radicals are, for example, imides, lactams and sulfoimides.

Examples of heterocyclic aromatic and heterocyclic radicals are: pyridyl, pyrimidinyl, pyrazinyl, triazinyl, furanyl, pyrrolyl, thiophenyl, quinolyl, isoquinolyl, coumarinyl, benzofuranyl, benzimidazolyl, benzoxazolyl, dibenzofuranyl, benzothiophenyl, dibenzothiophenyl, indolyl, carbazolyl, pyrazolyl, pyrazinyl, imidazolyl, oxazolyl, isoxazolyl, thiazolyl, indazolyl, benzothiazolyl, pyridazinyl, cinnolinyl, quinazolyl, quinoxalyl, phthalazinyl, phthalazinedionyl, phthalimidyl, chromonyl, naphtholactamyl, benzopyridonyl, orthosulfobenzimidyl, maleimidyl, naphtharidinyl, benzimidazolonyl, benzoxazolinyl, benzothiazolonyl, benzothiazolinyl, quinazolonyl, quinoxazolinyl, phthalazonyl, dioxapyrimidinyl, pyridonyl, isoquinolonyl, isothiazolyl, benzisoxazolyl, benzisothiazolyl, indazolonyl, acridinyl, acridonyl, quinazolinedionyl, benzoxazinedionyl, benzoxazinonyl and naphthalimidyl.

The aromatic or heterocyclic aromatic or heterocyclic radicals $R^1$, $R^2$, $R^3$ and/or $R^4$ can also have one or more non-water-solubilising substituents, in particular for example those listed below under a to r:

a) Halogen atoms, for example chlorine, bromine, iodine or fluorine.

b) Branched or unbranched alkyl groups preferably having 1 to 18, in particular 1 to 12, above all 1 to 8 and particularly preferably 1 to 4 C atoms. These alkyl groups can have one or more non-water-solubilising substituents, such as, for example, halogen, in particular fluorine, in addition hydroxyl, cyano, —OCOR$^5$, —OR$^6$, —OCOOR$^5$, —CON(R$^6$) (R$^7$) or —OCONHR$^5$, in which R$^5$ denotes alkyl, unsubstituted or, preferably, substituted aryl, such as naphthyl, and in particular benzyl which is unsubstituted or substituted by halogen, alkyl or —O—alkyl, or a heterocyclic radical. R$^6$ and R$^7$ denote hydrogen, alkyl which is unsubstituted or substituted by cyano or hydroxyl, unsubstituted or substituted C$_3$— and C$_{24}$—cycloalkyl, unsubstituted or substituted aryl or heteroaryl, in particular phenyl which is unsubstituted or substituted by halogen, alkyl or —O—alkyl, or R$^6$ and R$^7$ denote, in each case together with one of the other radicals R$^2$ to R$^4$, a 5- or 6-membered ring or, alternatively, a heteroring, such as, for example, a pyridine, pyrrole, furan or pyran ring. Other possible substituents on the alkyl groups are mono- or dialkylated amino groups, unsubstituted or substituted aryl, such as naphthyl or, in particular, phenyl which is unsubstituted or substituted by halogen, alkyl or —O—alkyl, or in addition heterocyclic aromatic radicals, such as, for example, the 2-thienyl, 2-benzoxazolyl, 2-benzothiazolyl, 2-benzimidazolyl, 6-benzimidazolonyl, 2-, 3- or 4-pyridinyl, 2-, 4- or 6-quinolyl or 1-, 3-, 4-, 6- or 8-isoquinolyl radicals.

If, in turn, the substituents mentioned under b) again contain alkyl, this alkyl can also be branched or unbranched and can preferably contain 1 to 18, in particular 1 to 12, above all 1 to 8 and particularly preferably 1 to 4 C atoms.

Examples of unsubstituted and substituted alkyl groups b) are methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl or benzyl.

c) The group —OR$^8$ in which R$^8$ denotes hydrogen, substituted or, preferably, unsubstituted alkyl, substituted or, preferably, unsubstituted C$_3$ to C$_{24}$-cycloalkyl, preferably C$_5$-, C$_8$-, C$_{12}$-, C$_{15}$-, C$_{18}$-, C$_{20}$- and C$_{24}$--cycloalkyl, substituted or preferably unsubstituted aryl, for example naphthyl, in particular phenyl which is unsubstituted or substituted by halogen, alkyl or —O—alkyl, or substituted or, preferably, unsubstituted heteroaryl. Alkyl occurring in the definitions of R$^8$ can have, for example, a number of C atoms indicated as preferred under b). Examples of R$^8$ which may be mentioned are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosany, thienyl or pyranylmethyl.

e) The cyano group.

f) The group of the formula —N(R$^6$)(R$^7$) in which R$^6$ and R$^7$ have the meaning indicated under b). Examples which may be mentioned are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecylamino, cyclopentadecylamino, cyclohexadecylamino, cycloeicosanylamino, cyclotetracosanylamino, phenylamino, N-methylphenylamino, benzylamino, dibenzylamino, piperidyl or morpholyl.

g) The group of the formula —COR$^5$ in which R$^5$ has the meaning indicated under b). Examples for R$^5$ which may be mentioned are: methyl, ethyl, n-propyl, isopropyl, n-butyl, sec-butyl, tert-butyl, tert-amyl, n-hexyl, 1,1,3,3-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m- or p-methylphenyl, 1- or 2-naphthyl, cyclophenyl, cyclohexyl, cyclododecyl, cyclopentadecyl, cyclohexadecyl, cycloeicosanyl, cyclotetracosanyl, thienyl, pyranylmethyl, benzyl or furfuryl.

h) The group of the formula —N($R^9$)COR$^5$ in which R$^5$ has the meaning indicated under b) and R$^9$ denotes hydrogen, alkyl, for example methyl, ethyl, n-propyl, isopropyl, n-butyl, sec-butyl, n-hexyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, cyanomethyl, methoxycarbonylmethyl, acetoxymethyl, benzyl, phenyl, in particular phenyl which is unsubstituted or substituted by halogen, alkyl or —O—alkyl, for example o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl, benzyl or furfuryl. Alkyl occurring in the definition of R$^9$ can have, for example, a number of C atoms indicated as preferred under b). Example [sic] which may be mentioned are: acetylamino, propionylamino, butyrylamino, benzoylamino, p-chlorobenzoylamino, p-methylbenzoylamino, N-methylacetamido, N-methylbenzoylamino, N-succinimido, N-phthalimido or N-(4-amino)phthalimido.

i) The group of the formula —N($R^8$)COOR$^5$ in which R$^5$ have [sic] the meaning indicated under b) or c). Examples which may be mentioned are the groups —NHCOOCH$_3$, —NHCOOC$_2$H$_5$ or —NHCOOC$_6$H$_5$.

j) The group of the formula —N($R^8$)CON($R^6$)($R^7$) in which R$^6$, R$^7$ and R$^8$ have the meaning indicated under b) or c). Examples which may be mentioned are: ureido, N-methylureido, N-phenylureido or N,N'-2', 4'-dimethylphenylureido.

k) The group of the formula —NHSO$_2$R$^5$ in which R$^5$ has the meaning indicated under b). Examples which may be mentioned are: methylsulfonylamino, phenylsulfonylamino, p-tolylsulfonylamino or 2-naphthylsulfonylamino.

l) The group of the formula —SO$_2$R$^5$ or —SOR$^5$ in which R$^5$ has the meaning indicated under b). Examples which may be mentioned are: methylsulfonyl, ethylsulfonyl, phenylsulfonyl, 2-naphthylsulfonyl or phenylsulfoxidyl.

m) The group of the formula —SO$_2$OR$^5$ in which R$^5$ has the meaning indicated under b). Examples which may be mentioned are: methyl, ethyl, phenyl, o-, m- or p-chlorophenyl, o-, m- or p-methylphenyl, 1-or 2-naphthyl.

n) The group of the formula —CON($R^6$)($R^7$) in which R$^6$ and R$^7$ have the meaning indicated under b). Examples which may be mentioned are: carbamoyl, N-methylcarbamoyl, N-ethylcarbamoyl, N-phenylcarbamoyl, N,N-dimethylcarbamoyl, N-methyl-N-phenylcarbamoyl, N-1-naphthylcarbamoyl or N-piperidylcarbamoyl.

o) The group of the formula —SO$_2$N($R^6$) (R$_7$) in which R$^6$ and R$^7$ have the meaning indicated under b). Examples which may be mentioned are: sulfamoyl, N-methylsulfamoyl, N-ethylsulfamoyl, N-phenylsulfamoyl, N-methyl-N-phenylsulfamoyl or N-morpholylsulfamoyl.

p) The group of the formula —N=N—R$^{10}$ in which R$^{10}$ denotes the radical of a coupling component or a phenyl radical which is optionally substituted by halogen, alkyl or —O—alkyl. Alkyl occurring in the definitions of R$^{10}$ can have, for example, a number of C atoms indicated as preferred under b). Examples of R$^{10}$ which may be mentioned are: the acetoacetarylide, pyrazolyl, pyridonyl, o- or p-hydroxyphenyl, o-hydroxynaphthyl, p-aminophenyl or p-N,N-dimethylaminophenyl radicals.

q) The group of the formula —OCOR$^5$ in which R$^5$ has the meaning indicated under b). Examples of R$^5$ which may be mentioned are: methyl, ethyl, phenyl, or o-, m- or p-chlorophenyl.

r) The group of the formula —OCONHR$^5$ in which R$^5$ has the meaning indicated under a). Examples of R$^5$ which may be mentioned are: methyl, ethyl, phenyl, or o-, m- or p-chlorophenyl.

Possible non-water-solubilising radicals R$^1$, R$^2$, R$^3$ and/or R$^4$ are in particular those which are indicated above under b) to r).

Compounds of the general formula I are preferably used in which one to three of the radicals R$^1$, R$^2$, R$^3$ and R$^4$ denote hydrogen, optionally substituted aromatic, optionally substituted heterocyclic aromatic and/or optionally substituted heterocyclic radicals and the remaining radical or the remaining radicals denote non-water-solubilising substituents, in particular those which are listed above under b to r.

Those compounds of the formula I are also preferred in which R$^3$ and/or R$^4$ denote aromatic or heterocyclic aromatic radicals which can also be substituted, in particular in the manner indicated, and in which R$^1$ and/or R$^4$ above all denote hydrogen, alkyl having 1 to 4 C atoms, phenyl or tolyl. The aromatic radicals here are in particular phenyl radicals which can also be trisubstituted or above all disubstituted and preferably monosubstituted by chlorine, methyl and/or methoxy. The heterocyclic aromatic radicals here are in particular pyridyl radicals, preferably 2-pyridyl radicals. Compounds of the general formula I are furthermore preferred in which R$^3$ and/or R$^4$ denote an optionally substituted aromatic radical, in particular phenyl, and R$^1$ and/or hydrogen or alkyl, in particular having 1 to 4 C atoms, and preferably methyl. The phenyl radical here is preferably monosubstituted by chlorine, methyl or methoxy or disubstituted by methyl and methoxy. R$^1$ and R$^2$ can be different or, preferably, identical. R$^3$ and R$^4$ can also be different or, preferably, identical.

Other dyes of the general formula I which are particularly highly suitable for their use in optical, in particular fluorescent memories, are indicated in Table 1 which follows:

TABLE 1

(I)

| No.: | R$^1$ = R$^2$ | R$^3$ = R$^4$ |
|---|---|---|
| 1 | H | phenyl |
| 2 | H | 4-tert. butylphenyl |
| 3 | H | 3,5-(tert. butyl)$_2$-phenyl |
| 4 | H | 2-CH$_3$-phenyl |
| 5 | CH$_3$ | 2-CH$_3$-phenyl |
| 6 | CH$_3$ | phenyl |

TABLE 1-continued

| No.: | R¹ = R² | R³ = R⁴ |
|------|---------|---------|
| 7    | $CH_3$  | 4-tert. butylphenyl |
| 8    | $CH_3$  | 3,5-(tert. butyl)$_2$-phenyl |

The preparation of the dyes indicated in the above table and their physical data are known, compare T. Potrawa and H. Langhals, Chem. Ber. 1920, 1075–1078 (1987).

Of the compounds of the formula I, particularly preferred compounds are those of the general formula Ia in which $R^1$ and $R^2$ are different or, preferably, identical and denote hydrogen, preferably alkyl having 1 to 4 C atoms, particularly preferably methyl, and $R^{13}$ and $R^{14}$ are different or, preferably, identical and denote hydrogen, alkyl having 1 to 4 C atoms, alkoxy having 1 to 4 C atoms, in particular methoxy, but where at least one of the radicals $R^{13}$ and $R^{14}$ must have a meaning different from hydrogen. Of the compounds of the formulae I and Ia, the particularly preferred compounds III and IV are suitable, above all, for the production of memories:

The compounds III and IV are novel and are claimed in the context of the present invention.

The radicals $R^{11}$ and $R^{12}$ can be different or, preferably, identical. The radicals $R^{11}$ and $R^{12}$ in particular have the meanings indicated for $R^1$ to $R^4$, with the exception of hydrogen. Those dyes of the formula II are preferred as storage media in optical memories, in which $R^{11}$ and $R^{12}$ denote phenyl radicals, which are substituted in their 4-positions by tert-butyl and at the same time in their 2-positions by halogen, such as, for example, chlorine, bromine or iodine. Of these dyes, the dyes of the formulae IIa and IIb are preferred. They are, like the dye of the formula IIc claimed in the context of the present invention. The preferred dyes of the formulae IIa and IIb can both each be transformed from a dark brown non-fluorescent form into a bright red form having a red fluorescence.

Those dyes of the formula II are furthermore preferred in which $R^{11}$ and $R^{12}$ denote cycloalkyl radicals having 3 to 24 C atoms, alkyl radicals having 1 to 35 C atoms, in particular 1 to 24 C atoms, naphthyl, anthryl or acridinyl, where the naphthyl, anthryl and acridinyl radicals can also be substituted, in particular by alkyl having 1 to 4 C atoms, preferably by tert-butyl. Those dyes of the formula II are also particularly preferred in which $R^{11}$ and $R^{12}$ are identical and denote secondary aliphatic radicals, in particular secondary alkyl radicals, above all those having 5 to 35 C atoms, in particular having 5 to 13 C atoms; preferably 3-pentyl, 4-heptyl, 5-nonyl, 6-undecyl, 7-tridecyl, 7-pentadecycl, 8-heptadecyl or 12-pentacosyl.

3,6 Bis (2'-methoxyphenyl)-2,5-dihydro-2,5-dimethyl-pyrrolo-(3,4-c)-pyrrole-1,4-dione of the formula III crystallises from organic solvents in an orange-colored form which only fluoresceses very slightly. This form is called IIIb in the following. If this form is heated to 195° to 200° C., it is rapidly transformed into a thermodynamically more stable yellow form IIIa which has an intense yellowish-green solid-state fluorescence. This thermal transformation is excellently suited for storage purposes. Of particular advantage here is the high stability of the dyes IIIa and IIIb. The photochemical stability of the dyes is also particularly high, as they have endured intensive solar irradiation for several months so far without any sign of a change. According to present knowledge, the dyes IIIa and IIIb can therefore be kept indefinitely. In particular, light-induced transformation of the orange-coloured form IIIb into the yellow form IIIa is not observed. This is important for a large number of reading cycles of an optical memory. The transformation enthalpy of IIIb into IIIa was determined and is $-1.5$ kcal/mol. As the reaction is exothermic, it will continue spontaneously after exceeding a critical temperature. This simplifies the writing process and makes it more secure against faults, since as a result a complete transformation of the dye into the other form and thus into the other logical state can easily be achieved. However, at $-15$ kcal/mol, the enthalpy set free is so small that no impairment whatsoever of a used matrix takes place owing to the development of heat and the transformation of a storage location is also not influenced by adjacent storage locations. The crystal lattices of both forms are very stable. The coloring of the substances and the reflections from X-ray powder photographs also do not change with intensive mechanical stress. The basic conditions for an optical fluorescent memory are thus fulfilled in a nearly ideal manner by the dye III.

Figure 1A:
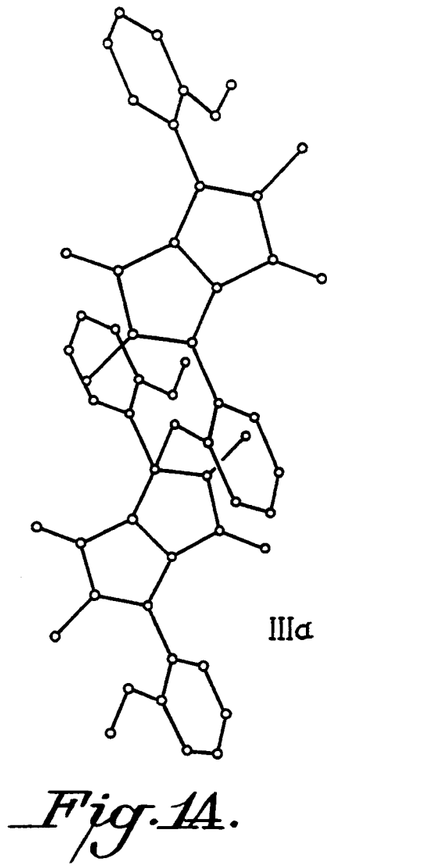
FIGS. 1a and 1b show dye structures IIIa and IIIb.
Figure 1B:
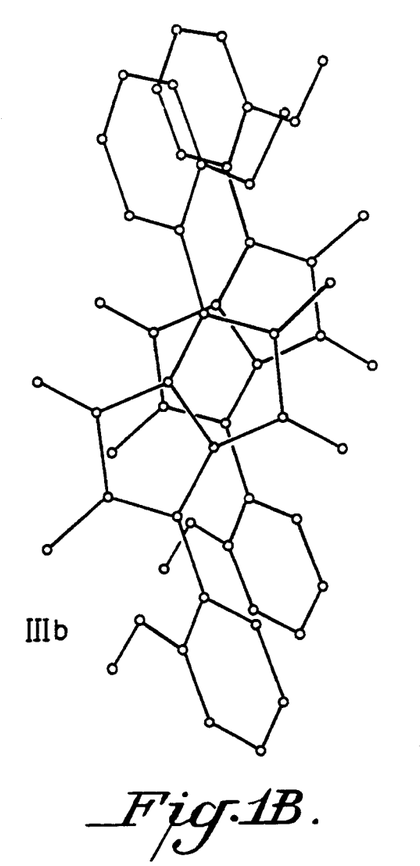

FIG. 1 shows the dye structures IIIa and IIIb.

According to X-ray crystal investigations, the forms IIIa and IIIb crystallise in monoclinic form. Their crystallographic densities differ only very slightly, In IIIa, the methoxy group is rotated with respect to the carbonyl group of the chromophore so that the o-anisyl radical is at an angle of 59° to the plane of the chromophore. In IIIb, the methoxy group is facing away from the carbonyl group, the corresponding angle here is 50°. In both crystal lattices, the chromophores are similarly stacked, in particular pairs of dimers are not found. Information about the interactions of the chromophore essential for fluorescence are obtained from X-ray structural analyses of the two forms. A section of the crystal lattice with a viewing direction perpendicular to the plane of the chromophore is indicated in FIG. 1. For the only weakly fluorescent, orange-coloured form IIIb, the chromophores therein are viewed laid directly one above the other. At a plane separation of only 3.81 Å an intense interaction of the chromophores occurs which on the one hand leads to a bathochromic shift of the absorption (orange-colour) and on the other causes a strong coupling of the electron excitation to lattice vibrations. Owing to the latter, the excitation energy discharges in lattice vibrations, and a solid-state fluorescence is largely quenched. In the form IIIa, in contrast, the chromophores are pushed strongly against one another so that a chromophore-chromophore interaction can only take place again with the next layer but one. However, this is already 6.18 Å removed—the interactions are therefore negligibly small. The essentially isolated chromophores now behave in the crystal as in dilute solution. They absorb at long wavelengths (yellow) and fluoresce strongly.

Against an intramolecular electron transfer from the methoxy group to the chromophore it can be said, on the one hand, that for IIIb, its separation from the carbonyl group is greater than for IIIa and, on the other hand, in solution no noticeable dependence of the fluorescence quantum yields on the solvent polarity is observed. The fluorescence quantum yields in chloroform and acetonitrile differ only slightly. The small separation and thus the relatively strong interactions of the chromophores in IIIb are also reflected in the solid absorption spectra again, as the orange-colored IIIb absorbs at a substantially longer wavelength than the yellow IIIa.

It is to be assumed that the small separation of the chromophores in IIIb does not only lead to a long-wave absorption, but also to a solid coupling of the electron system by lattice vibrations, since a periodic change in the chromophore separation causes a periodic change in the UV-VIS absorption or fluorescence spectrum. The electronic excitation energy can diskharge in lattice vibrations via the coupling. The process of internal conversion is thus promoted. In contrast, this fluorescence deactivation has no significance in the dye IIIa owing to the relatively large separation of the chromophores. The interaction is already small and is hardly influenced by lattice vibrations. This explains the strong solid fluorescence of the dye.

In a preferred optical fluorescent memory according to the invention, the substance or the dye to be used according to the invention having at least one fluorescent form is applied and fixed to the data carrier, for example a disk, or suspended in the data carrier. In particular, the memory is coated with the preferably used dye of the formula III, or it contains this dye. The information to be stored is then input, for example, using a laser beam, whereby a thermal transformation of the dye IIIb to the dye IIIa takes place. To read the information, the disk is scanned, for example, with a laser beam which excites the dye IIIa to fluorescence in the transformed locations. The detection can take place simply by formation of the image of the fluorescent point on a light-sensitive receiver. The decay time of the fluorescence is so brief at about $10^{-8}$ to $10^{-9}$s that it can be read at high frequency.

A fluorescent memory of this type can be recorded once and then read very frequently. In the present form, however, there is no possibility of erasing it. However, erasable memories are preferred, in particular in computer technology.

Erasable optical memories, in particular fluorescent memories, can also be produced using substances to be used according to the invention, in particular using the dye of the formula III.

In order to erase a recorded optical fluorescent memory made, for example, using the dye III as a memory, the dye IIIa must be transformed again into the form IIIb. In order to achieve this, the great tendency to crystallise of the form IIIb can be utilised, as the dye III spontaneously crystallises from homogeneous solution in the thermodynamically unfavourable form IIIb. If the dye is now mixed with a thermally stable auxiliary substance which melts at a sufficiently high temperature, for example a little above the transformation point, of about 170° to 190° C., then this melt can dissolve the dye. On cooling, IIIb then crystallises out, and the thermally input storage point is again erased. The high-melting auxiliary substance should be thermally stable. High-melting aromatic compounds, for example, are suitable as an auxiliary substance of this type.

Anthracene, in particular high-purity anthracene, and in particular terphenyl, are particularly highly suitable as a high-melting auxiliary substance. Anthracene, for example, does not form mixed crystals with the dye III. If, for example, the dye III in the form IIIb is mixed with anthracene in the weight ratio 1:5, an orange-coloured powder is obtained in which the dye does not fluoresce or only fluoresces very weakly. If this mixture is now heated to temperatures of 170° to 195° C., then the form IIIb is transformed into IIIa in the solid state, and the substance fluoresces strongly yellowish green. The transformation, which now corresponds to the inputting of information, can now be read by means of the fluorescence. If the mixture is then heated further to above 220° C., i.e. to above the melting point of anthracene, then the anthracene melts and dissolves the dye III, irrespective of whether it is present in the form IIIa or IIIb. On cooling, the non-fluorescent form IIIb then crystallises out. The information is erased again. This cycle can be run through many times without changing the dye or the anthracene as auxiliary or matrix and is only limited by the thermal long-term stability of the components.

Anthracene is very highly suitable as a material for the auxiliary substance or the matrix, as on the one hand it can be prepared easily in a highly pure form by chromatographic filtration with chloroform on alumina and on the other hand it is sufficiently thermally stable and inert as an aromatic hydrocarbon. Moreover, its melting point is in the optimum temperature range. Terphenyl is also particularly highly suitable as an auxiliary. Other aromatic hydrocarbons can also be employed as an auxiliary substance or matrix material after possible suitable substitution. Heterocycles are also suitable for this purpose. Other examples of suitable high temperature-stable aromatic hydrocarbons are: biphenyl, guaterphenyl and linear and branched polyphenylenes having a degree of polymerisation of at least 3 to 500, preferably 3 to 50, highly preferably 3 to 10. The hydrocarbons naphthalene, phenanthrene, triphenylene, chrysene, 3,4-benzophenanthrene, 1,2-benzochrysene, picene, 5,6-benzochrysene, 3.4,5.6-dibenzophenanthrene, hexahelicene, 1.2,7.8-dibenzochrysene, 11.12,13.14-dibenzopicene, 1.2,3.4,5.6,-7.8,9.10,11.12-hexabenzotriphenylene, tetraphene, 1.2,3.4-di-benzanthracene, 1.2,5.6-dibenzanthracene, 1.2,7.8-dibenzanthracene, 1.2,3.4,5.6-tribenzanthracene, 1.2,3.4,5.6,7.8-tetrabenzanthracene, 1.2-benzotetraphene, 3.4-benzotetraphene, 3.4,8.9dibenzotetraphene, pentaphene, 3.4-benzopentaphene, 3.4,9.10-dibenzopentaphene, 1.2,5.6-dibenzotetraphene, 6.7-benzopentaphene, dinaphtho-(2′,1′:1,2);(2″,1″:5,6)-antracene, naphtho-(2′,3′:6,7)-pentaphene, naphtho-(2′,3′:3,4)-pentaphene, naphtho-(2′,3′:3,4)-pentaphene, naphtho-(2′3′:3,4)-pentaphene, anthraceno-(2′,1′:1,2)-anthracene, anthraceno-(2′1′:8,9)-tetraphene, tetrapheno-(8′,9′:8, 9)-tetraphene, 2,3-benzopicene, 2.3,8.9-dibenzopicene, anthraceno-(1′,2:1,2)-tetraphene, fluorene, biphenylene, 1.2-benzobiphenylene, 2.3-benzobiphenylene, 1.2,7.8-dibenzobiphenylene, 2.3,6.7-dibenzobiphenylene, tetraphenylene, pentaphenylene, hexaphenylene, octaphenylene, perylene, 1,12-benzoperylene, coronene, pyrene, 1.2-benzopyrene, 3.4-benzopyrene, fluoranthene, 2.3-benzofluoranthene, 2.3-benzofluoranthene, 10.11-benzofluoranthene, 11.12-benzofluoranthene, 9.10,11.12-dibenzofluoranthene, 2.13-benzofluoranthene, 4.5-o-phenylenfluoranthene, isorubicene, 10.11-(peri-naphthylene)fluoranthene, 11.12-(perinaphthylene) fluoranthene and decacyclene are additionally preferred. These aromatic compounds and anthracene and terphenyl can in turn again carry 1 to 4 of the radicals mentioned under a) to r). Substituted, appropriately high-melting derivatives of benzene are also suitable. Partially crystalline or liquid crystalline polymers, for example, silicone polymers, or perfluoroethers containing aromatic groups are additionally suitable as auxiliary substances.

The high temperature-stable auxiliary substances can be used individually or as mixtures having a suitable melting point.

A further possibility for the production of an erasable optical fluorescent memory consists in embedding the dye which is fluorescent in one form, in particular the dye of the formula III, not in a high-melting substance, but in a poorly dissolving high-boiling liquid as a medium which only dissolves the dye slightly at room temperature and even at the temperature of the transformation, but then dissolving this at relatively high temperatures, about 300° C. for the dye III. On cooling, the thermodynamically unfavourable form IIIb then also crystallises out again, as a result of which, such as for anthracene, the information is erased. However, the strong fluorescence of the dye in solution is problematical here, so that only very few poorly dissolving liquids are suitable. Oligomeric perfluoroethers which can also be mixed with oligomeric polytrifluorochloroethylene, have proved to be particularly favourable here. The following are also suitable: polytetrafluoroethylenes, ethylenes, in particular those having a degree of polymerization 10 to 100,000, perfluoropolyether oils, in particular those having a degree of polymerisation of 10 to 100,000, a mixture of perfluoropolyether oil and polyvinylidene fluoride having degrees of polymerisation of 10 to 100,000 and silicone oils and silicone resins.

The optical memories according to the invention as the storage medium contain a substance, in particular a solid substance, above all a dye, having at least two, preferably two, differently colored forms, one form of which can be transformed into a differently coloured form by supplying energy, for example in the form of ultrasound, heat or, preferably, light. Fluorescent memories are preferred which contain a substance which is fluorescent in at least one modification, in particular a dye, preferably the dye III, IIa or IIb, as the storage medium. Memories are very particularly preferred which cannot only be recorded once and then read as often as desired, but which also can be erased again. Particularly preferred memories according to the invention of this type contain substances to be used according to the invention as a storage medium which can be transformed from one form into a differently coloured form not only by supplying energy, but which can also be transformed from the second to the first form again. Erasable, in particular fluorescent, memories of this type contain the storage medium if possible together with an auxiliary substance or an auxiliary substance mixture of the type already mentioned.

Inorganic glasses, for example, such as, for example, silicate, phosphate or borate glasses, amorphous silica, organic glasses, such as, for example, polymethacrylate or polycarbonates or, alternatively, other materials which may also be partially crystalline such as polyvinyl chloride, polystyrene, polyethylene, polypropylene, polyvinylidene chloride, polyesters and polyamides can be used as carriers for the substances to be used according to the invention.

The substances to be used according to the invention in particular dyes, can, for example, be applied and fixed to a carrier in a suitable manner. The application is carried out, for example, using the screen-printing process or using evaporation techniques, expediently in a specific pattern, so that separate memory locations are present which can easily be addressed separately and later read again. To apply the substances, in particular dyes, in a specific pattern on a carrier and then their subsequently fix them on the carrier, however, still other techniques are also suitable, in particular crystallisation from a solution of a substance in an organic solvent. In this case, an organic solvent of the type which has a melting point above the transformation point of the utilised substance is in particular used as a medium and this then dissolves in the molten state. An organic solvent of the type which in the molten state dissolves the substance is in particular used as a medium, but on cooling it is allowed to crystallise out in a metastable form. A medium of this type are, for example, anthracene and terphenyl.

The substances to be used according to the invention as storage media can also be suspended in the carrier or be contained in the carrier in another manner.

It is expedient to incorporate the substances to be used as memories in said carrier materials or to apply to the carrier materials in a very uniform particle or crystal size, for example in the range from 0.1 to 200 μm, preferably from 0.1 to 50 μm, and very particularly preferably from 1 to 10 μm.

The memories according to the invention consisting of the carrier and the storage medium to be used according to the invention and, if appropriate, auxiliary or auxiliary mixture can have, for example, the form of a rotatable disk, such as is used in disk systems, or they can alternatively form, for example, a stationary plate. Fluorescent memories are preferred which contain a dye fluorescing in at least one form, and preferably only in one form, in particular the dye III, IIa or IIb. Memories according to the invention contain the substances to be used as storage media on a suitable carrier or in a suitable carrier, possibly together with an auxiliary substance, such as anthracene or terphenyl, or an auxiliary substance mixture. Information can be input by supplying energy, in particular thermal energy or light energy, to the substances used as storage medium present in or on the carrier. The thermal energy can be supplied, for example, by means of thermoprinter systems. However, the inputting of the information preferably takes place using a laser beam. Reading taking place after inputting the information can be carried out with the aid of a laser beam, the absorption of the dyes used being used as a criterion for storage. During the reading of the information using a laser beam, however, the fluorescence of the dyes used is preferably used as a storage criterion. In this case, the emerging fluorescent light can be focussed by known methods onto a light-sensitive electronic component. The emerging fluorescent light can also be filtered such that no scattered light from the exciting light beam falls on the receiver of the fluorescent light. Non-erasable and erasable optical memories of this type can be used, for example, in EDP systems, in particular mass memories of computers, text processing equipment, image processing equipment and image recording systems or in audio storage systems, such as, for example, preferably digital disk players, or in video systems, preferably in video recorders and video disks, or in holographic systems.

For reading erasable optical fluorescent memories, a laser is required which emits at the absorption of the dye, i.e., for example, a wavelength of about 515 nm or less. Lasers having this wavelength range are available. In order to simplify the system further, semiconductor lasers can be used which heat up the surrounding matrix during the writing process with their intense IR radiation. During the reading process, the frequency of the laser can be doubled in a known manner by connecting a crystal into the light path so that light having the half wavelength for exciting the fluorescence is now obtained using a lower intensity. On using the shorter wavelength of the light, a greater resolving power is obtained during data storage.

The use of those substances, in particular dyes of the formulae I or II, which incorporate the solvent molecules in the crystal lattice offers another possibility for the construction of fluorescent memories. At high temperature, this solvent is then liberated again, and the dye and possibly also the fluorescence is changed.

The red dye IV, for example, fluoresces intensively reddish-orange. By contrast, recrystallised from solvents, such as, for example, methanol or acetone, orange-coloured crystals, for example, having a yellowish-orange solid-state fluorescence are obtained which have the solvent, for example methanol, incorporated in the crystal lattice. The dye indicated in Table 1 under the number 7 is orange and fluoresces weakly orange. Table 2 which follows indicates the dye and the solid fluorescence which the dye has if it has been recrystallised from the solvents indicated in Table 2 and contains these solvents incorporated in the crystal lattice:

TABLE 2

| Solvent | Dye | Solid fluorescence |
| --- | --- | --- |
| Nitrobenzene | pink | weak |
| Acetone | orange | yellow |
| Methanol | pale orange | intensely yellowish-orange |
| tert.-butyl methyl ether | pale orange | intensely yellowish-orange |

The dye indicated in Table 1 under the number 3 is dark red and fluoresces weakly red. Table 3 which follows indicates the dye and fluorescence which the dye has if it has been recrystallised from the solvents indicated in Table 3 and contains these solvents incorporated in the crystal lattice:

TABLE 3

| Solvent | Dye | Solid fluorescence |
| --- | --- | --- |
| Acetone | pink | — |

TABLE 3-continued

| Solvent | Dye | Solid fluorescence |
| --- | --- | --- |
| Methanol | orange | intensively yellowish-orange |
| tert.-amyl alcohol | orange | yellowish-orange |
| ethyl acetate | reddish-orange | — |
| pinacolone | reddish-orange | — |
| i-propanol | yellow | yellow |
| dioxane | yellow | — |

Dyes which obtain another colour and/or another fluorescence by the incorporation of solvents into the crystal lattice can be used in optical memories which are recorded once. The solvent is given off in the recording process.

The dye of the formula II where $R^{11}=R^{12}=5$-nonyl ($=$N,N'di(5-nonyl)perylene-3,4:9,10-tetracarboxylic acid bismide) crystallises from solutions in an intensely pale orange fluorescent form. On warming to about 200° C., it is transformed irreversibly into the moderately-red fluorescent form. As the dye always crystallises out of solution in the pale form, the involvement of the solvent in the transformation is improbable.

Dyes of the formula II where $R^{11}=R^{12}=7$-pentadecyl, 8-heptadecyl or 12-pentacosyl are only obtained from n-pentane at low temperatures ($-30°$ to $0°$ C.) as pale orange crystals which in some cases are already transformed into the dark red forms at 50° to 60° C. The inclusion of 0.5 to 1 mol of solvent, which is liberated again on warming, is calculated here. The transformation is irreversible.

BRIEF DESCRIPTION OF THE DRAWINGS

Fluorescent memories which can be recorded and erased and are preferred according to the invention are shown by way of example and schematically in FIGS. 2 and 3.

Figure 2:
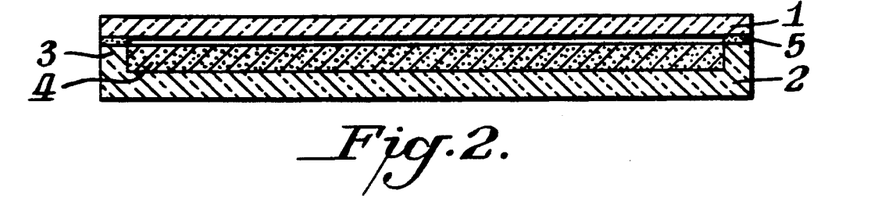

FIG. 2 shows a vertical section through a memory in the form of a round plate or disk. This is composed from the upper disk 1 and lower disk 2, which has a circumferential raised edge 3. As a result, a dish is formed in which, for example, a mixture of the dye III and one of the said auxiliary substances, such as, for example, highest-purity anthracene, for example in the weight ratio 1:5, is poured. In FIG. 2 this mixture is indicated by 4. The upper disk 1 is then placed on the edge 3 of the lower disk 2 and firmly connected to it, for example glued (5). At least one of the disks 1 and 2 consists of an optically transparent material. The disks 1 and 2 can consist, for example, of glass. By heating to, for example, 220° C., the mixture 4 becomes molten, and the thermodynamically metastable form IIIb of the dye III crystallises out of the melt on cooling. The memory can now be recorded, read and, if desired, also erased again in the manner already described.

Figure 3:
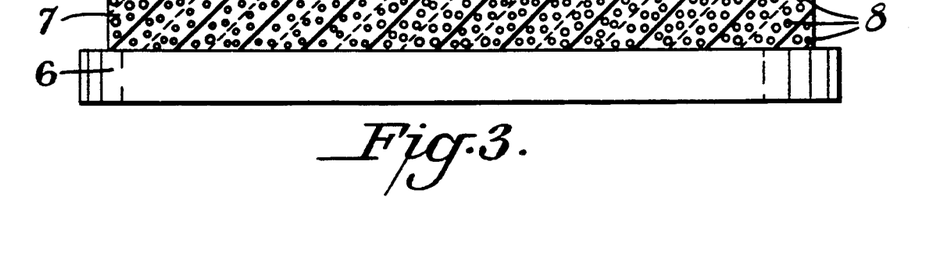

FIG. 3 shows a vertical section through another memory in the form of a plate or disk. This consists of the carrier 6, to which a layer 7 is applied. This layer 7 consists of an optically transparent plastic, for example of polyamide or polyimide, in which uniformly distributed fine particles, in particular spherules 8 are incorporated. These particles or spherules 8 consist, for example, of a mixture of anthracene or terphenyl and a suitable dye, such as, for example, the dye III. The particles or spherules 8 are uniformly distributed in the plastic, and the plastic containing the spherules is applied to the carrier 6, which can be carried out, for example, in a centrifugal process. If desired, the layer can additionally be covered by a covering layer (not shown in FIG. 3) made of optically transparent material, for example a suitable plastic. The memory shown diagrammatically in FIG. 3 can be recorded, read and erased in the manner already mentioned.

With an optical fluorescent memory according to the invention, during focussing of the reading light beam onto the memory element formed from a fluorescent dye, the fluorescence takes place nearly isotropically in all spatial directions; the memory element to be read itself becomes the light source. As the addressing of the storage elements is determined spatially and chronologically by the excitation beam, comparatively simple optics suffice for the detection system. Optical inhomogeneities in the storage element additionally only affect its readability very slightly. Moreover, the light emission takes place at a longer wavelength than the excitation owing to the Stokes shift of the fluorescent dyes. Uncontrolled reflections of the excitation light can as a result be filtered out in a simple manner. The susceptibility of the system to interference is as a result lowered further still. The storage density attainable with the optical memories according to the invention is virtually only limited by the light wavelength used for loading or reading. The attainable storage density is therefore high. The optical memories according to the invention have a high long-term stability and, as a result and as no partial erasure takes place owing to the reading process, enable a virtually unlimited number of reading cycles. The reading speed is high (100 MHz to 16 GHz, corresponding to 1 to 10 ns). The writing and erasure rate is average to high.

Compounds of the general formula I are for the largest part known. Compounds of the formula I in which $R^1$ and $R^2$ denote hydrogen and $R^3$ and $R^4$ denote identical or different isocyclic or heterocyclic aromatic radicals are also known as red pigments from EP-B1-61,426. The aromatic radicals $R^3$ and $R^4$ in the compounds of EP-B1-61,426 can also contain one or more non-water-solubilising substituents.

Compounds of the general formula I in which $R^3$ and $R^4$ denote aromatic or heterocyclic radicals and $R^1$ and $R^2$ independently of one another denote non-water-solubilising substituents, where $R^3$ and $R^4$ can also be hydrogen, are known from EP-A3 133,156 as polymer-soluble dyes or pigments for high molecular-weight organic material.

The compounds of the general formula I can be prepared by various processes which are known per se. According to the process described in EP-B1-61,426, a nitrile of the formula $R^3CN$ is reacted, if desired together with a nitrile of the formula $R^4CN$ bromoacetic ester and zinc, a compound of the formula I where $R^1=R^2=H$ being formed. Better yields are obtained if 2 mol of the nitrile $R^3CN$ or the nitrile mixture $R^3CN/R^4CN$ are reacted in a manner known per se with 1 mol of a diethyl succinate in an organic solvent in the presence of a strong base at elevated temperature, cf. EP-B1-94,911 and T. Potrawa and H. Langhals, Chem. Ber. 1920, 1075–1078 (1987).

A particularly favourable process for the preparation of the compounds of the general formula I consists in reacting furanofurandione of the general formula V (V)

with a primary amine of the general formula $R^1NH_2$ or with a mixture of primary amines $R^1NH_2/R^2NH_2$. In this formula, $R^1$, $R^2$, $R^3$ and $R^4$ have the meanings already mentioned. (If $R^1$ and/or $R^2$ denote hydrogen, the primary amine $R^1NH_2$ or $R^2NH_2$ is ammonia. Compounds of the formula I where $R^1$ and/or $R^2=H$ are then obtained. The ammonia can also be employed fn the form of compounds which eliminate ammonia).

The reaction between the compound of the general formula V and the primary amine or the mixture of primary amines is expediently carried out in a suitable inert solvent or dispersant.

Suitable solvents or dispersants are, for example, ethers, in particular those having 2 to 8 C atoms in the molecule, such as, for example, diethyl ether, methyl ethyl ether, di-n-propyl ether, diisopropyl ether, methyl n-butyl ether, methyl tert-butyl ether, ethyl n-propyl ether, di-n-butyl ether, tetrahydrofuran, 1,4-dioxane, 1,2-dimethoxyethane, bis-β-methoxyethyl ether; oligoethylene glycol dimethyl ethers, such as, for example, pentaglyme; aliphatic hydrocarbons, such as, for example, hexane, heptane, low- and high-boiling petroleum ethers; cycloaliphatic hydrocarbons, such as, for example, cyclohexane, methylcyclohexane, tetralin, decalin; aromatic hydrocarbons, such as, for example, benzene, toluene, o-, m- and p-xylene, ethylbenzene; halogenated aliphatic or aromatic hydrocarbons, such as, for example, methylene chloride, chloroform, carbon tetrachloride, chlorobenzene, dichlorobenzene; nitriles, such as, for example, acetonitrile; amides, such as, for example, dimethylformamide, dimethylacetamide, N-methylpyrrolidone; hexamethylphosphoric triamide; and sulfoxides, such as, for example, dimethyl sulfoxide. Mixtures of various solvents can also be used.

The reaction is preferably carried out in a dipolar aprotic solvent. Examples of preferred dipolar aprotic solvents are: dimethylformamide, dimethyl sulfoxide, hexamethylphosphoric triamide, sulfolane, N-methylpyrrolidone, tetramethylurea, acetonitrile, ethylene glycol dimethyl ether, ethylene glycol diethyl ether, diethylene glycol dimethyl ether and triethylene glycol dimethyl ether, nitromethane, 1,3-dimethyl-3,4,5,6-tetrahydro-2(1H)-pyrimidinone (DMPU). 1,3-dimethyl-2-imidazolidinone, benzonitrile, nitrobenzene, chloroform, carbon tetrachloride and methylene chloride. Particularly preferred dipolar aprotic solvents are chloroform, carbon tetrachloride and methylene chloride, of which chloroform is very particularly preferred.

It is furthermore expedient to carry out the reaction between the compound of the general formula V and the primary amine, or the mixture of primary amines, in the presence of a dehydrating agent. Examples of suitable dehydrating or water-eliminating agents of this type are: N,N'-disubstituted carbodiimides, in particular if they contain at least one secondary or tertiary alkyl radical, such as, for example, diisopropyl-, dicyclohexyl- or N-methyl-N'-tert. butylcarbodiimide (cf. Methodicum Chimicum, Verlag G. Thieme, Stuttgart, Vol. 7, (1974), pp. 682/683, and Ruben-Weyl, Methoden der Org. Chemie (Methods of Organic Chemistry), Vol. 8, (1952), pp. 521/522). Dicyclohexylcarbodiimide is very particularly suitable.

The reaction between the compound of the formula V and the primary amine $R^1NH_2$ or the mixture of the primary amines $R^1NH_2/R^2NH_2$ can be carried out, for example, at temperatures from $-10°$ C. up to the boiling point of the solvent or solvent mixture used. In many cases it is carried out at 10° to 30° C. and preferably at room temperature. 1.9 to 2.4 mol, preferably 2.0 to 2.3 mol of the primary amine $R^1NH_2$ or of the mixture of primary amines $R^1NH_2/R^2NH_2$ are expediently employed per mole of furanofurandione of the general formula V.

The starting compounds of the general formula V and the primary amines $R^1NH_2$ and $R^2NH_2$ are known or can be easily prepared by the methods known for the preparation of these classes of compound.

Other processes for the preparation of compounds of the general formula I are known and, for example, described in EP-A3-133,156 (page 10 et seq.), EP-A3-181,290 and EP-98,808.

In one of these processes, which is particularly suitable for the preparation of the compounds of the formula I, in particular of the formula Ia and preferably of the formula III and IV, a lactam of the formula VI (VI)

in which R, for example, denotes a lower alkyl radical, in particular ethyl, and $R^3$ has the meaning already mentioned, is reacted with a nitrile of the formula $R^4CN$ in which $R^4$ has the meaning already mentioned, cf. EP-13-181290 page 2. The lactam of the formula VI is easily accessible via the acylsuccinic acid ester VIII in a manner known per se, for example starting from the dicarbonyl compound VII (VII)          (VIII)

If compounds of the general formula I where $R^1=R^2=H$ are formed by said process, these compounds can be transformed in a manner known per se into compounds of the formula I where $R^1$ and/or $R^2$ are not equal to hydrogen by reaction with one of the radicals $R^1$ or $R^2$ (where $R^1$ and $R^2$ have the meanings already mentioned with the exception of hydrogen) as compounds containing leaving groups, expediently in a suitable inert solvent. Processes for the introduction of the radicals $R^3$ and $R^4$ (unequal to hydrogen) into compounds of the formula I where $R^3=R^4=$hydrogen are described, for example, in T. Potrawa and H. Langhals, Chem. Ber. loc. cit. and EP-13-133158. Suitable alkylating agents are, for example, alkyl halides, in particular alkyl iodides, alkyl esters, in particular alkyl esters of sulfonic acids, such as, for example, alkyl esters of benzene- or p-toluenesulfonic acid.

The compounds of the formula I and II can be purified particularly advantageously by extractive recrystallisation according to the process described by H. Langhals in Chem. Ber. 118, (1985), 4641. In this process, the extract is continuously and centrally fed back into the contents of the extraction flask without cooling of the extraction flask contents occurring as a result.

Perylene-bis-dicarboximides of the general formula II in which $R^{11}=R^{12}$ are also known to a large extent, cf., for example, A. Rademacher, S. Markle and H. Langhals in Chem. Ber. 15, 2977–2934 (1982); H. Langhals in Chem. Ber. 18, 4641–4645 (1985); DE-B-1,130,099, DOS 2,139,688, 2,147,024, 2,210,170, 2,451,784, GB Patent 901,694.

The dye of the formula II where $R^{11}=R^{12}=5$-nonyl is very particularly preferred.

The dyes of the formula II can be prepared, for example, by heating perylene-3,4:9,10-tetracarboxylic acid bisanhydride at temperatures of 180° to 220° C. with an amine $R^{11}NH_2$ or a mixture of two amines $R^{11}NH_2/R^{12}NH_2$ in the presence of zinc acetate and quinoline or imidazole under a protective gas atmosphere.

The optical memories and the dyes of the general formulae I and II, in particular the dyes of the formulae Ia, III, IV, IIa and IIb, according to the invention, can be generally employed for marking purposes, preferably for security markings. The advantage here is that in a carrier coated uniformly or non-uniformly with dye, for example the dye IIIb, information can be input by supplying thermal energy or light energy and can then be recognised and read under UV irradiation via the fluorescence. The inputting can be carried out using a laser beam or in still simpler systems using a thermoprinter/plotter. A pattern can also be produced very rapidly rapidly and easily in the applied dye layer by thermal means. This is also important for machine-readable printing on documents, as owing to the controlled excitation there is less susceptibility, for example to corruption, when reading a fluorescent marking than a dyeing based on absorption. A substrate correspondingly pretreated with dyes of the formulae I or II can be, for example, a sheet of paper or a plastic film in which fluorescent information, for example a character is entered thermally using a laser beam or a thermo-printer-plotter. This is of interest, for example, for constructing a security marking which is specific in each case, for commercial purposes, for the labelling of products for later sorting processes and for a large number of other applications. Examples additionally to be mentioned are machine-readable markings, preferably alphanumeric printings and bar-codes.

Dyes of the formulae I and II which show a strong solid fluorescence as such or after recrystallisation from an organic solvent can also frequently be employed as fluorescent pigments, i.e., for example, as signal dyes, for example, for visually emphasising characters and diagrams or other graphical products, for the marking of signs and other objects in which it is intended to achieve a particular visual impression; as a security marking on cheque cards or other objects in which it is intended to achieve a particular unmistakable dye impression; as an additive to other dyes in which it is intended to achieve a specific colour shade as a result of the fluorescence, i.e., for example, a particularly bright color shade is a marking of objects which are intended to be recognised and sorted mechanically and in which the recognition is intended to take place by means of the fluorescence (an example of this is the recycling of plastics which can be sorted with the aid of the fluorescence); as a fluorescent dye for machine-readable markings; as a component of toners for electrophotography (®Xerox process, laser prints) in order to obtain fluorescent prints; for artistic applications and purposes; use in scintillators; use generally for the frequency conversion of light, for example in order to make longer-wave visible light from short-wave light; use as a fluorophore in lighting and display components, for example in fluorescent tubes, in Braun's tubes and in fluorescent displays; use of the dyes in passive display components for various display, reference and marking purposes, for example passive display components, information and road signs, such as traffic lights; use in ink jet printers (it is particularly advantageous that a section of the dyes, i.e., for example, the dye of the formula II where $R^{11}=R^{12}=5$-nonyl also crystallises out from homogeneous solution in strongly fluorescent form without particular control of the physical conditions. This is of particular interest for applications in ink jet printers, as the dye can then be homogeneously dissolved and after dyeing and subsequent drying reliably gives a fluorescent spot of colour).

The dyes which are also particularly suitable as solid fluorescent pigments because of their particularly strong solid fluorescence are above all the dye of the formula II where $R^{11}=R^{12}=5$-nonyl, and additionally the dyes of the formula I3 listed in Table 4 which follows

TABLE 4

(I)

| $R^1=R^2$ | $R^3=R^4$ | Fluorescence |
|---|---|---|
| H | $C_6H_5$ | weakly red |
| H | $2\text{-}CH_3\text{—}C_6H_4$ | orange |
| $CH_3$ | $2\text{-}CH_3\text{—}C_6H_4$ | bright green |
| $C_2H_5$ | $2\text{-}CH_3\text{—}C_6H_4$ | bright green |
| $CH_2\text{—}C_6H_5$ | $4\text{-}t\text{-}C_4H_9\text{—}C_6H_4$ | weakly orange |
| $CH_3$ | $3,5\text{-}di\text{-}t\text{-}C_4H_9\text{—}C_6H_3$ | bright orange |
| $C_6H_5$ | $C_6H_5$ | bright pink |
| $4\text{-}CH_3\text{—}C_6H_4$ | $C_6H_5$ | bright pink |

A dye, which after recrystallising from a solvent, i.e. after the incorporation of a solvent in the crystal lattice, has a particularly strong solid-state fluorescence, for example, the dyes of the formula II where $R^1=R^2=H$ and $R^3=R^4=3,5$-di-tert-butyl and where $R^1=R^2=CH_3$ and $R^3=R^4=4$-tertbutylphenyl.

Dyes of the general formula I and/or II can also be used as thermochromic temperature probes. Use as an overheating control of equipment may be mentioned as an example.

EXAMPLE 1

3,6-Bis(2'-methoxyphenyl)-2,5-dihydropyrrolo(3,4-c)-pyrrole-1,4-dione a) 12.0 g (48.6 mmol) of 3-methoxycarbonyl-2-(2'-methoxyphenyl)-2-pyrrolin-5-one, 28.0 g (249 mmol) of potassium tert-butylate and 14.0 g (105 mmol) of 2-methoxybenzonitrile are kept under gentle reflux in 100 ml of tert-amyl alcohol under nitrogen and with continuous stirring for three days. After cooling to about 60° C., first 100 ml of methanol and then 20 ml of glacial acetic acid are added. The precipitated product is filtered with suction through a glass frit (G4) and washed several times with methanol.

Yield 11.89 g (70.2%) of dark red powder.
Melting point 336°–337° C. dec. (from toluene).
$R_f$(silica gel-toluene/acetone=4:1).
UV (DMF): $\lambda_{max}$ (1 g $\epsilon$)=525 nm (4.496), 489 nm (4,397), 460 nm (sh).
Fluorescence (DMF): $\lambda_{max}$=533 nm, 575 nm.
$C_{20}H_{16}N_2O_4$ (348.3) Calc.: C, 68.95; H, 4.62; N, 8.04. Found: C, 68.47; H, 4.51; N, 8.24.

b) The 3-methoxycarbonyl-2-(2'-methoxyphenyl)-2-pyrrolin-5-one needed as a starting product can be prepared as follows:

2-Methoxyacetophenone 250 g (1.98 mol) of dimethyl sulfate is added dropwise to a mixture of 130 g of potassium hydroxide in 1.1 of water and 260 g (1.90 mol) of 2-hydroxyacetophenone with cooling and vigorous stirring in such a way that the reaction solution is not heated above 40° C. After the reaction temperature has then been kept at 80° C. for 30 minutes, the mixture is allowed to cool to room temperature and extracted by shaking with a total of 250 ml of chloroform. The organic phase is shaken three times with 100 ml of 2N sodium hydroxide solution each time and dried over sodium sulfate. After filtration and removal of the solvent on a rotary evaporator, the oil obtained is distilled in vacuo.

Yield 223.7 g (78.4%) of colorless liquid, Boiling point 121°–124° C./21.28 mbar.

Methyl 2-methoxybenzoylacetate 58.5 g (1.08 mol) of sodium ethanolate are added to 500 ml of dimethyl carbonate. The mixture is then heated to boiling and traces of methanol are removed by distillation. 153.5 g (1.02 mol) of 2-methoxyacetophenone are allowed to drip in at 86° C. with vigorous stirring during the course of 4.5 hours. (If the reaction mixture becomes too viscous, a further addition of dimethyl carbonate is recommended.) The mixture is then subsequently stirred for a further 30 minutes and the solvent is removed by distillation under reduced pressure. After cooling to room temperature, 350 ml of water and 70 ml of glacial acetic acid are added and the mixture is stirred overnight. The oil formed is separated off and the aqueous phase is extracted by shaking with a total of 300 ml of ethyl acetate. The combined organic phases are first washed with a 6% strength sodium hydrogen carbonate solution (100 ml), then with a sodium chloride solution (the sodium chloride promotes the phase separation). After drying the ethyl acetate phase over sodium sulfate, filtration and after removing the solvent on a rotary evaporator, the remaining oil is distilled in a high vacuum.

Yield 92.7 g (43%) of yellowish oil, boiling point 118°–119° C./0.01 mbar, $n_D^{20}$=1.5401.

Dimethyl 2-methoxybenzoylsuccinate 91.16 g (440 mmol) of methyl 2-methoxybenzoylacetate, 57.5 g (530 mmol) of methyl chloroacetate, 280 ml of acetone, 190 ml of dimethoxyethane and 70.0 g (510 mmol) of potassium carbonate are boiled under reflux for 22 hours. After cooling to room temperature, the mixture is filtered with suction and the residue is washed with n-hexane. The combined filtrates are concentrated on a rotary evaporator and 70 ml of methanol are added to the oil which remains. After a short time, the dimethyl 2-methoxybenzoylsuccinate crystallises out.

Yield 73.7 g (59.0%) of colorless crystals, melting point 75°–76° C. (methanol), $R_f$(silica gel/ethyl acetate)=0.83.
$C_{14}H_{16}O_6$(280.2) Calc.: C, 59.99; H 5.75.
Found: C 60.28; H 5.75.

3-methoxycarbonyl-2-(2'-methoxyphenyl)-2-pyrrolin-5-one 152.5 g (1.98 mol) of ammonium acetate and 50.0 g (0.18 mol) of dimethyl 2-methoxybenzoylsuccinate are boiled under reflux for two hours in 175 ml of glacial acetic acid (oil bath 120°–130° C.). The cooled dark green reaction mixture is allowed to drip into about 500 ml of ice-water with stirring. After filtering with suction and drying over calcium chloride, a pea-green powder is obtained (melting point 163°–167° C.) which is directly employed for the subsequent reaction.

Yield 37.4 g (84%), melting point 165°–166° C. (from methanol), $R_f$(silica gel/ethyl acetate)=0.74.
$C_{13}H_{13}NO_4$ (247.2) Cal: C, 63.15; H, 5.67; N, 5.67.
Found: C, 63.45; H, 5.42; N, 5.41.

EXAMPLE 2

3,6-Bis(2'-methoxyphenyl)-2,5-dihydropyrrolo(3,4-c)-pyrrole-1,4-dione 12.51 g (93.95 mmol) of 2-methoxybenzonitrile, 10.75 g of potassium tert-butylate and 9.57 g (46.8 mmol) of diisopropyl succinate are reacted analogously to the directions in Chem. Ber. 120, 1075–1078 (1987) and the mixture is worked up.

Yield 400 mg (2.4%) of dark red iridescent crystals.
Melting point 336°–337° C. (dec. from toluene).

EXAMPLE 3

2,6-Bis(2'-methoxyphenyl)-2,5-dihydro-2,5-dimethyl-pyrrolo(3,4-c)pyrrole-1,4-dione 400 mg (1.14 mmol) of 3,6-Bis(2'-methoxyphenyl-2,5-dihydropyrrolo-(3,4-c)pyrrole-1,4-dione [sic] and 2.08 g (11.2 mmol) of methyl p-toluenesulfonate are reacted with 1.2 g of potassium carbonate in 5 ml of DMF analogously to the directions in Chem. Ber. 120, 1075–1078 (1987) and the mixture is worked up.

Yield 360 mg (84%) of orange-colored crystals (IIIb).

Transformation point 195° C., melting point 281°–282° C. (from ethanol/chloroform 3:1).
$R_f$(tert-butyl methyl ether)=0.44.
UV(CHCl$_3$): $\lambda_{max}$(lg $\epsilon$)=454 nm(4.206). Fluorescence (CHCl$_3$):$\epsilon_{max}$=514 nm.
Fluorescence quantum yield: $\phi$(CHCl$_3$)=0.68, $\phi$(CH$_3$CN)=0.59.
IIIa: $C_{22}H_{20}N_2O_4$ (376.4) Cal.: C, 70.20; H, 5.35; N, 7.44. Found: C, 69.90; H, 5.31; N, 7.47.
IIIb: $C_{22}H_{20}N_2O_4$ (376.4) Cal.: C, 70.20; H, 5.35; N, 7.44. Found: C, 70.17; H, 5.29; N, 7.46.

EXAMPLE 4

3,6-Bis(2'-methoxyphenyl)-2,5-dihydro-2,5-dimethyl-pyrrolo(3,4-c)pyrrole-1,4-dione 570 mg methyl iodide (0.25 ml=4.0 mmol) are added at room temperature with stirring to a mixture of 500 mg (1.5 mmol) of 3,6-bis(2'-methoxyphenyl)-2,5-dihydropyrrolo(3,4-c)pyrrol-1,4-dione and 1.5 g of KOH (27 mmol) in 25 ml of DMF. After about 3 minutes, the product begins to precipitate out of the reaction solution, and after a further 5 minutes 60 ml of ice-water are added. The orange-yellow precipitate was filtered with suction, washed with water and dried.

Yield 420 mg (75%), melting point 281°–282° C. (ethanol/chloroform 3:1).

EXAMPLE 5

3-(2'-Methoxyphenyl)-6-phenyl-2,5-dihydropyrrolo(3,4-c)-pyrrole-1,4-dione 3.0 g (12.1 mmol) of 3-methoxycarbonyl2-(2'-methoxyphenyl)-2-pyrrolin-5-one [sic], 7.00 g (62.3 mmol) of potassium tert-butylate and 2.50 g (24.2 mmol) of benzonitrile are kept under gentle reflux in 25 ml of tert-amyl alcohol under nitrogen and with continuous stirring for 24 hours. After cooling to about 60° C., first 25 ml of methanol, then 2.5 ml of glacial acetic acid are added. The precipitated product is filtered off with suction through a glass frit (G4) and washed several times with methanol.

Yield 3.04 g (78.3%) of red powder, which can be directly further reacted. For purification, it can be extractively recrystallised from toluene.

Melting point 355°–356° C., R$_f$(silica gel/toluene: acetone=4:1)=0.68.

UV (DMF): $\lambda_{max}$(1 g $\epsilon$)=514 nm (4.516).

Fluorescence (DMF): $\lambda_{max}$=525 nm $C_{19}H_{14}N_2O_3$(318.3) Calc.: C, 71.69; H, 4.43; N, 8.80. Found: C, 71.61; H, 4.38; N, 8.92.

EXAMPLE 6

3-(2'-Methoxyphenyl)-6-phenyl-2,5-dihydro-2,5-dimethylpyrrolo(3,4-c)pyrrole-1,4-dione a) 400 mg (1.25 mmol) of 3-(2'-methoxyphenyl)-6-phenyl-2,5-dihydropyrrolo(3,4-c)pyrrole-1,4-dione are reacted analogously to Example 4 and the mixture is worked up.

Yield 0.33 g (75%), melting point 177°–178° C., R$_f$ (silica gel/tert-butyl methyl ether)=0.62.

UV (CHCl$_3$): $\lambda_{max}$(1 g $\epsilon$)=464 nm (4.224).

Fluorescence (CHCl$_3$): $\lambda_{max}$=518 nm.

$C_{21}H_{18}N_2O_3$ (346.3) Calc.: C, 72.82; H, 5.24; N, 8.09. Found; C, 73.04; H, 5.29; N, 89.27.

b) A yellowish orange fluorescent compound containing methanol as the guest molecule is obtained by recrystallisation of the product obtained according to a) from methanol/chloroform:

$C_{21}H_{18}N_2O_3 \cdot 0.5CH_3OH$ (362.4) Calc.: C, 71.26; H, 5.56; N, 7.73. Found: C, 71.06; H, 5.62; N, 7.85.

EXAMPLE 7

3,6-Bis(2'-methylphenyl)2,5-dihydro-2,5-diethylpyrolo-(3,4-c)pyrrole-1,4-dione 1.23 g (33.89 mmol) of 3,6-Bis (2'-methylphenyl)-2,5-dihydropyrrolo(3,4-c)pyrrole-1,4-dione in 100 ml of DMF and 4.0 g of potassium carbonate are reacted with 8.32 g (38.3 mmol) of ethyl p-toluenesulfonate in 20 ml of DMF. Yield 300 mg (21%) of yellowish-green crystals having intense solid fluorescence.

Melting point 265°–267° C. ( from toluene).

R$_f$(silica gel/toluene, acetone 4:1)=0.69.

UV(CHCl$_3$[sic]: $\lambda_{max}$(1 g $\epsilon$)=436 nm.

Fluorescence (CHCl$_3$): $\lambda_{max}$=488 nm.

$C_{24}H_{24}N_2O_2$ (372.46) Calc.: C, 77.39; H, 6.49; N, 7.52. Found: C, 77.42; H, 6.45; N, 7.31.

EXAMPLE 8

3,6-Bis(2'-chlorophenyl)-2,5-dihydropyrrolo(3,4-c)pyrrole-1,4-dione 13.25 g (96 mmol) of 2-chlorobenzonitrile and 11.5 g (102 mmol) of potassium tert-butylate in 20 ml of tert-amyl alcohol are reacted with 8.71 g (49.3 mmol) of diethyl succinate in 20 ml of tert-amyl alcohol. Yield 1.1 g (6.9%) of violet powder (recrystallised extractively from isopropyl alcohol by the process described by H. Langhals in Chem. Ber. 118, (1985), 4641).

Melting point>360° C.

UV(CHCl$_3$): $\lambda_{max}$=497 nm, 479-fluorescence [sic] (CHCl$_3$): $\lambda_{max}$=518 nm.

EXAMPLE 9

3,6-Bis(2'-chlorophenyl)-2,5-dihydro-2,5-dimethylpyrrolo(3,4-c)-pyrrole-1,4-dione 1.00 g (2.79 mmol) of 3,6-Bis(2'-chlorophenyl)-2,5-dihydropyrrolo(3,4-c)pyrrole-1,4-dione and 2.0 g of potassium carbonate in 50 ml of DMF are reacted with 5.71 g (30.00 mmol) of methyl p-toluenesulfonate in 10 ml of DMF.

Yield 380 mg (35.2%) of brownish-red crystals.

Melting point 268°–270° C. (from ethanol, toluene).

R$_f$(silica gel/toluene, acetone 4:1)=0.59).

UV(CHCl$_3$): $\lambda_{max}$ (1 g $\epsilon$)=441 nm (4.153).

Fluorescence (CHCl$_3$): $\lambda_{max}$=506 nm.

EXAMPLE 10

3,6-Bis(2-pyridinyl)-2,5-dihydro-2,5-dimethylpyrrolo(3,4-c)-pyrrole-1,4-dione 1.00 g (3.44 mmol) of 3,6-Bis(2-pyridinyl)-2,5-dihydropyrrolo(3,4-c)pyrrole-1,4-dione and 1.9 g of potassium carbonate in 25 ml of DMF are reacted with 1.49 g (8.00 mmol) of p-toluenesulfonic acid ester in 5 ml of DMF.

Yield 990 mg (91.4%) of violet crystals.

Melting point 289°–290° C. (from chloroform).

R$_f$(silica gel/toluene, acetone 4:1)=0.70.

UV(CHCl$_3$): $\lambda_{max}$ (1 g $\epsilon$)=516 nm (4.257), 491 nm (4.211).

—UV(Ethanol): $\lambda_{max}$(1 g $\epsilon$)=510 nm (4.058), 488 nm (4.039).—

Fluorescence (CHCl$_3$): $\lambda_{max}$=543 nm.

$C_{18}H_{14}N_4O_2$ (318.32) Calc.: C, 67.91; H, 4.43; N, 17.60. Found: C, 68.03; H, 4.28; N, 17.58.

EXAMPLE 11

3,6-Bis(2-pyridinyl)-2,5-dihydro-2,5-diethylpyrrolo(3,4-c)pyrrole-1,4-dione 1.00 g (3.44 mmol ) of 3,6-Bis(2-pyridinyl)-2,5-dihydropyrrolo(3,4-c)pyrrole-1,4-dione and 1.9 g of potassium carbonate are reacted with 2.00 g (9.98 mmol) of ethyl p-toluenesulfonate in 7.5 ml of DMF.

Yield 970 mg (81.4%) of dark violet crystals.

Melting point 244°–245° C. (from CHCl$_3$/ethanol) .

R$_f$(silica gel/toluene, acetone 4:1)=0.67).

UV(CHCl$_3$): $\lambda_{max}$ (1 g $\epsilon$)=519 nm (4.231), 495 nm (4.192).

—Fluorescence (CHCl$_3$): $\lambda_{max}$=545 nm.

$C_{20}H_{18}N_4O_2$ (346.38) Calc.: C, 69.35; H, 5.23; N, 16.17. Found: C, 69.18; H, 5.23; N, 16.27.

EXAMPLE 12

3,6-Bis(2'-methyl-4'-methoxyphenyl)-2,5-dihydropyrrolo(3,4-c)-pyrrole-1,4-dione 36.79 g (250 mmol) of 2-methyl-4-methoxybenzonitrile and 28.05 g of potassium tert-butylate in 60 ml of tert-amyl alcohol are reacted with 25.28 g (125 mmol) of diisopropyl succinate in 10 ml of tert-amyl alcohol.

Yield 1.82 g (3.86%) of orange powder. Purification is carried out by extractive recrystallisation from toluene by the process described by H. Langhals in Chem. Ber. 118, (1985), 4641.

Melting point 319° C. (dec.). = $R_f$ (silica gel/CHCl$_3$) = 0.17.

UV(DMSO): $\lambda_{max}$ (1 g $\epsilon$) = 460 nm (4,405).

Fluorescence (DMSO): $\lambda_{max}$ = 519 nm.

$C_{22}H_{20}N_2O_4$ (376.39) Calc.: C, 70.20; H, 5.35; N, 7.44. Found: C, 70.20; H, 5.46; N, 7.24.

EXAMPLE 13

2,5-Dihydro-2,5-diphenyl-3,6-diphenylpyrrolo(3,4-c)pyrrole-1,4-dione 200 mg (0.69 mmol) of 3,6-diphenylfurano(3,4-c)furan-1,4-dione were allowed to stand at room temperature for 3 days with 170 mg (0.82 mmol) of dicyclohexylcarbodiimide and 153 g (1.65 mmol) of aniline in 30 ml of chloroform. Purification of the reaction product was carried out by extractive recrystallisation from toluene by the process described by H. Langhals in Chem. Ber. 118, (1985), 4641.

Yield 170 mg (46.0%) of pink needles having an intense orange solid fluorescence.

Melting point > 360° C.

$R_f$(silica gel/CHCl$_3$) = 0.24.

UV(CHCl$_3$): $\lambda_{max}$ (1 g $\epsilon$) = 484 nm (3.941), 464 nm (3.923).

Fluorescence (CHCl$_3$): $\lambda_{max}$ = 520 nm, 555 nm (sh).

$C_{30}H_{20}N_2O_4$ (440.4) Calc.: C, 81.81; H, 4.50; N, 6.45. Found: C, 81.51; H, 4.47; N, 6.36.

EXAMPLE 14

2,5-Dihydro-2,5-bis(4'-methylphenyl-3,6-diphenylpyrrolo(3,4-c)pyrrole-1,4-dione 240 mg (0.83 mmol) of 3,6-diphenylfurano(3,4-c)furan-1,4-dione, 445 mg (2.13 mmol) of dicyclohexylcarbodiimide and 400 mg (4.20 mmol) of p-toluidine in 30 ml of chloroform are allowed to stand at room temperature for 3 days. Purification is carried out by extractive recrystallisation from toluene by the process described by H. Langhals in Chem. Ber. 118, (1985), 4641.

Yield 100 mg (26%) of orange needles having an intense solid fluorescence.

Melting point > 360° C. $R_f$(silica gel/CHCl$_3$) = 0.22.

UV(CHCl$_3$): $\lambda_{max}$ (1 g $\epsilon$) = 488 nm (4.357), 470 nm (4.330).

Fluorescence (CHCl$_3$): $\lambda_{max}$32 521 nm, 549 nm (sh).

$C_{32}H_{24}N_2O_2$ (468.6) Calc.: C, 82.03; H, 5.16; N, 5.98. Found: C, 81.80; H, 5.09; N, 5.95.

EXAMPLE 15

2,5-Dihydro-2-phenyl-3,6-diphenylpyrrolo(3,4-c)furan-1,4-dione 250 mg (0.86 mmol) of 3,6-diphenylfurano(3,4-c)furan-1,4-dione, 444 mg (2.13 mmol) of dicyclohexylcarbodiimide and 401 mg (4.31 mmol) of aniline in 30 ml of chloroform were allowed to stand at room temperature for 6 hours. The course of the reaction was monitored by TLC chromatography [sic]. The reaction product was separated by column chromatography.

Yield 15 mg (4.8%) of orange-coloured powder. It was possible to obtain a further 60 mg of 2,5-dihydro-2,5-diphenyl-3,6-diphenylpyrrolo(3,4-c)pyrrole-1,4-dione as an afterfraction.

Melting point 230°–232° C.

$R_f$(silica gel/CHCl$_3$) = 0.47.

UV(ChCl$_3$)[sic]: $\lambda_{max}$ (1 g $\epsilon$) = 472 nm (4.287), 449 nm (4.309).

Fluorescence (CHCl$_3$): $\lambda_{max}$ = 498 nm, 524 nm.

EXAMPLE 16

General directions for the preparation of 3,4:9,10-perylenebis(dicarboximide)s:

a) Method A:

1.0 g (2.5 mmol) of perylene-3,4:9,10-tetracarboxylic acid bisanhydride are mixed with 10 mmol of the amine concerned and 350 mg of zinc acetate. After addition of 5 ml of freshly distilled quinoline, the mixture is heated to 220° C. under reflux under an $N_2$ protective atmosphere for 4 h. After cooling, 5 ml of water and 80 ml of ethanol are added and the mixture is then allowed to stand for at least 4 h. The precipitated solid is filtered off with suction through a D 4 glass frit and washed with ethanol. After drying the solid is recrystallised extractively with toluene (H. Langhals, Chem. Ber. 118, 4641 (1985)).

The compounds prepared by this method are indicated in Examples 17 to 37 of the two following Tables 5 and 6.

b) Method B:

1.0 g (2.5 mmol) of perylene-3,4:9,10-tetracarboxylic acid bisanhydride [sic] are heated to 180° C. for 4 h with 5 mmol of the amine concerned and 350 mg of zinc acetate and also 5 g of imidazole under an $N_2$ protective atmosphere and the mixture is then worked up as described for method A. The reaction temperature can be varied within wide limits in method B.

The compounds of the following Examples 17 to 37 of the following Table 5 are prepared by method A of Example 16. The molecular formulae and analyses are indicated in Table 6.

(II)

TABLE 5

| No.: | $R^{11}=R^{12}$ | Yield[a] % | Rf[b] |
|---|---|---|---|
| 17 | dodecyl | 80 | 0.33 |
| 18 | cyclopropyl | 22 | 0.06 |
| 19 | cyclononyl | 66 | 0.57 |

TABLE 5-continued

| No.: | R¹¹=R¹² | Yield[a] % | Rf[b] |
|---|---|---|---|
| 20 | cyclodecyl | 40 | 0.63 |
| 21 | cycloundecyl | 50 | 0.64 |
| 22 | cyclotridecyl | 80 | |
| 23 | cyclotetradecyl | 80 | |
| 24 | cyclopentadecyl | 80 | |
| 25 | 2-propyl | | 0.13 |
| 26 | 3-pentyl | 80 | 0.27 |
| 27 | 4-heptyl | 80 | 0.41 |
| 28 | 5-nonyl | 80[e] | 0.50 |
| 29 | 6-undecyl | 80[f] | 0.58 |
| 30 | 7-tridecyl | 80[g] | 0.61 |
| 31 | 1-naphthyl | 5 | 0.16 |
| 32 | 1-(3,6-di-tert-butylnaphthyl | 36 | 0.47 |
| 33 | 1-(3,7-di-tert-butylnaphthyl) | 37 | 0.92 |
| 34 | 1-anthryl | 2 | |
| 35 | 1-(2-tert-butyl-anthryl) | 2 | 0.42 |
| 36 | 9-acridinyl | 9 | 0.60[c] |
| 37 | 9-(2-tert-butyl-acridinyl) | 44 | 0.76[d] |

[a]isolated yields of analytically pure substance
[b]chloroform/silica gel
[c]1,2-dichloroethane
[d]ethanol
[e]melting point 280° C.
[f]melting point 184° C.
[g]melting point 157–158° C.

TABLE 6

| No. | Molecular formula (molecular weight) | | Elemental analysis | | |
|---|---|---|---|---|---|
| | | | C | H | N |
| 17 | C₄₈H₅₈N₂O₄ (727.0) | Calc. | 79.30 | 8.40 | 3.85 |
| | | Found | 79.33 | 8.10 | 3.84 |
| 18 | C₃₀H₁₈N₂O₄ (470.5) | Calc. | 76.59 | 3.86 | 5.95 |
| | | Found | 76.40 | 3.95 | 5.70 |
| 19 | C₄₂H₄₂N₂O₄ (638.8) | Calc. | 78.97 | 6.63 | 4.39 |
| | | Found | 79.14 | 6.69 | 4.13 |
| 20 | C₄₄H₄₆N₂O₄ (666.9) | Calc. | 79.25 | 6.95 | 4.20 |
| | | Found | 79.22 | 6.85 | 4.25 |
| 21 | C₄₆H₅₀N₂O₄ (694.9) | Calc. | 79.51 | 7.25 | 4.03 |
| | | Found | 79.22 | 7.07 | 4.13 |
| 22 | C₅₀H₅₈N₂O₄ (751.0) | Calc. | 79.96 | 7.78 | 3.73 |
| | | Found | 79.76 | 7.59 | 3.55 |
| 23 | C₅₂H₆₂N₂O₄ (779.1) | Calc. | 80.17 | 8.02 | 3.60 |
| | | Found | 80.36 | 8.05 | 3.73 |
| 24 | C₅₂H₆₆N₂O₄ (807.13) | Calc. | 80.36 | 8.24 | 3.47 |
| | | Found | 80.30 | 8.15 | 3.69 |
| 26 | C₃₄H₃₀N₂O₄ (530.6) | Calc. | 76.96 | 5.70 | 5.28 |
| | | Found | 77.21 | 5.68 | |
| 27 | C₃₈H₃₈N₂O₄ (586.7) | Calc. | 77.79 | 6.53 | 4.77 |
| | | Found | 77.67 | 6.31 | 4.64 |
| 28 | C₄₂H₄₆N₂O₄ (642.8) | Calc. | 78.47 | 7.21 | 4.36 |
| | | Found | 78.58 | 7.13 | 4.18 |
| 28 | C₄₆H₅₄N₂O₄ (698.9) | Calc. | 79.05 | 7.79 | 4.01 |
| | | Found | 78.50 | 7.66 | 4.08 |
| 30 | C₅₀H₆₂N₂O₄ (755.05) | Calc. | 79.54 | 8.28 | 3.71 |
| | | Found | 79.67 | 8.36 | 3.81 |
| 31 | C₄₄H₂₂N₂O₄ (642.8) | Calc. | 82.23 | 3.45 | 4.36 |
| | | Found | 82.13 | 3.51 | 4.42 |
| 32 | C₆₀H₅₄N₂O₄ (867.1) | Calc. | 83.11 | 6.28 | 3.23 |
| | | Found | 83.23 | 6.27 | 3.12 |
| 33 | C₆₀H₅₄N₂O₄ (867.1) | Calc. | 83.11 | 6.28 | 3.23 |
| | | Found | 83.23 | 6.39 | 3.25 |
| 34 | C₅₂H₂₆N₂O₄ (742.8) | Calc. | 84.08 | 3.53 | 3.77 |
| | | Found | 83.86 | 3.65 | 3.88 |
| 35 | C₆₀H₄₂N₂O₄ (855.0) | Calc. | 84.29 | 4.95 | 3.28 |
| | | Found | 84.38 | 5.12 | 3.30 |
| 36 | C₅₀H₂₄N₂O₄ (744.8) | Calc. | 80.64 | 3.25 | 7.52 |
| | | Found | 80.39 | 3.51 | 7.54 |
| 37 | C₅₈H₄₀N₂O₄ (857.0) | Calc. | 81.29 | 4.70 | 6.54 |
| | | Found | 80.31 | 4.46 | 6.26 |

EXAMPLE 38

N,N'-Bis(4-tert-butyl-2-iodophenyl)perylene-3,4:9,10-biscarboximide a) 3.0 g (11 mmol) of 4-tert-butyl-2-iodoaniline are heated at 145° C. for five hours together with 1.1 g (2.8 mmol) of perylene-3,4:9,10-tetracarboxylic acid bisanhydride, 10 g of imidazole and 0.5 of zinc acetate dihydrate. After cooling, 80 ml of ethanol and 4 ml of water are added to the reaction mixture and it is stirred overnight. The mixture is filtered off through a porosity 4 glass filter crucible. The solid product mixture is chromatographed:

Column (80 cm, φ4.5 cm) 300 g of silica gel 60/CHCl₃.

Ten 500 ml fractions are taken off and in each case concentrated to 30 to 50 ml. Of these, fractions two to four are combined and trickled in the dark through a porosity 4 glass suction filter and then dried in the dark.

Melting point: above 360° C.

C₄₄H₃₂I₂N₂O₄ (906.6) Calc.: C, 58.30; H, 3.56. Found: C, 54.99; H, 3.58.

The transformation of the dark brown non-fluorescent form into the bright red form having a red fluorescence takes place at more than 250° C.

b) The 4-tert-butyl-2-iodoaniline needed as a starting material can be prepared as follows:

54.40 g (215.0 mmol) of iodine are added to 35.00 g (234.5 mmol) of 4-tert-butylaniline and the mixture is stirred. The reaction is initially vigorous enough to lead to a distinct warming of the mixture. If this slackens, 60 ml of water, 60 ml of diethyl ether and 25 g of calcium carbonate are added and the reaction mixture is boiled under reflux until the black color of the iodine has disappeared. This mixture is subjected to steam distillation. Six liters of distillate are collected and then extracted by shaking three times with 25 ml of methylene chloride each time in six one liter portions. The organic phase is dried using sodium sulfate. This solution is concentrated and conc. hydrochloric acid is then added. Crude yield 14.05 g (19.25%). After recrystallisation from acetonitrile, 4-tert-butyl-2-iodoaniline hydrochloride results as colorless crystals.

Yield: 13.65 g (18.70%)

Sublimes from 150° C.

C₁₀H₁₅ClIN (311.6) Calc.: C, 38.55; H, 4.85; N, 4.50. Found C, 38.70; H, 4.85; N, 4.72.

The hydrochloride is stirred with 5 g of KOH and 300 ml of water. The mixture is extracted by shaking three times with 20 ml of methylene chloride each time and the organic phase is dried over sodium sulfate. After stripping off the methylene chloride, 10.87 g (16.00% based on the starting aniline) of 4-tert-butyl-2-iodoaniline result as a clear, slightly yellowish oil.

nD20: 1.5998

EXAMPLE 39

N,N'-Bis(2-bromo-4-tert-butylphenyl)-3,4:9,10-perylene-biscarboximide 0.9 g (4 mmol) of 2-bromo-4-tert-butylaniline are heated at 160° C. for three hours together with 0.4 g (1 mmol) of perylene-3,4:9,10-tetracarboxylic acid bisanhydride, 3.0 g of imidazole and 0.06 g of zinc acetate dihydrate. 140 ml of 60% ethanol are then added to the mixture and it is stirred for four hours. After filtering through a porosity 4 glass suction filter and drying, 0.94 g crude yield results.

This crude product is chromatographed: (column 80 cm, φ4.5 cm) 300 g of silica gel 60/CHCl₃. 24 500 ml fractions are taken off (and in each case concentrated to approximately 30 ml). According to the thin layer chromatograms, fractions 13 to 22 are pure (Rf=0.25, at high humidity).

Fractions 13 to 22 are combined, filtered through a porosity 4 glass suction filter in order to separate off silica gel, and then precipitated using pentane. The precipitated product is filtered with suction through a P4 glass suction filter and dried in an oil pump vacuum ($2.10^{-3}$ hectopascal). 0.03 g (3%) yield results.

$C_{44}H_{32}Br_2N_2O_4$ Calc: C, 65.04; H, 3.97; N, 3.0 Found: C, 64.12; H, 3.98; N, 3.21.

Possibly CHCl$_3$ is still occluded:

$C_{44}H_{32}O_4N_2Br_2 \cdot CHCl_3$ Calc.: C, 64.24; H, 3.92; N, 3.40. UV (CHCl$_3$): $\lambda_{max}(e) = 526$ nm (87704), 489 nm (50731), 458 nm (16337).

The transformation of the dark brown non-fluorescent form to the bright red form having a red fluorescence takes place at 110° to 115° C.

EXAMPLE 40

N,N'-Bis(4-tert-butyl-2-chlorophenyl)-3,4:9,10-perylene-biscarboximide 1.8 g (10 mmol) of 2-chloro-4-tert-butylaniline are heated at 170° C. for three hours with 0.97 g (2.5 mmol) of perylene-3,4:9,10-tetracarboxylic acid bisanhydride, 4.00 g of imidazole and 0.40 g of zinc acetate dihydrate. 100 ml ethanol and a little water are then added to the reaction mixture and it is stirred overnight. The solid is filtered off through a glass filter crucible of porosity 4 and washed with ethanol. This solid is boiled with 5% sodium carbonate solution and filtered off through a porosity 4 glass filter crucible. The precipitate is washed with hot sodium carbonate solution until the filtrate comes out colorless. The solid is extractively recrystallised with toluene by the method of H. Langhals in Chem. Ber. 118, (1985), 4641.

Crude yield: 1.05 g (58%).

This crude product is subjected to chromatography: (column 80 cm, $\phi$4.5 cm) 300 g of silica gel 60/chloroform.

Six fractions result which in each case are concentrated to about 30 ml. Silica gel 60/chloroform thin layer chromatography shows that all six fractions are non-uniform. Further chromatography is therefore carried out. However, the silica gel is previously moistened with 20 ml of water. This time 22 500 ml fractions are taken off and in each case concentrated to about 30 ml. From the thin layer chromatography, it turns out that fractions 5 to 9 only contain one substance. These fractions are filtered through a porosity 4 glass filter crucible in order to remove silica gel.

Yield: 11.19 mg 58.6%)
Melting point: above 360° C.
UV (CHCl$_3$): $\lambda_{max}(e)$ 526 nm (87690), 489 nm (52784), 457 nm (20006).

$C_{44}H_{32}O_4N_2Cl_2$ (723.66) Calc.: C, 73.03; H, 4.46. Found; C, 72.98; H, 5.12.

The dyes indicated in Examples 41 to 43 can be prepared by the following general procedure:

2.55 mmol of perylene-3,4:9,10-tetracarboxylic acid bisanhydride, 6 mmol of the amine hydrochloride concerned and 5 g of imidazole are heated to 160° C. under a nitrogen atmosphere for 1 h. The cooled reaction mixture is suspended in 100 ml of ethanol, 300 ml of 2N hydrochloric acid are added, the mixture is stirred at room temperature for 1 h and the dye is filtered off. The filter cake is suspended in 300 ml of 10% potassium carbonate solution. The suspension is boiled for 15 min and the solid is filtered off. The crude product is then dried at 100° C. for 8 h. For purification, the dye is dissolved in 10 ml of chloroform and purified through silica gel using chloroform in an 800 mm long and 40 mm thick column. The dye in this case is always the first and largest fraction. A green halo which may be present around the dye band is discarded. The dye fraction is concentrated on a rotary evaporator and recrystallised from n-pentane at low temperatures (to $-30°$ C.). Depending on the conditions, a red powder or pale orange crystals precipitate out here. The yields for the total synthesis were between 50 and 80%.

EXAMPLE 41

N,N'-Di(7-pentadecyl)perylene-3,4:9,10-tetracarboxylic acid bisimide

Melting point = 122° C.
UV (CHCl$_3$): $\lambda$max (e) = 458 nm (86040), 489 nm (51460), 525.5 nm (18670).
Fluorescence (CHCl$_3$): $\lambda$max = 534 nm, 576 nm.
Solid-state fluorescence, pale, orange form: $\lambda$max = 587 nm, 625 nm.
Solid-state fluorescence, dark, red form: $\lambda$max = 642 nm. Transformation range from pale to dark: 50°-60° C.

EXAMPLE 42

N,N'-Di(8-heptadecyl)perylene-3,4:9,10-tetracarboxylic acid bisimide

UV (CHCl$_3$): $\lambda$max = 457.5 nm, 488 nm, 525 nm.
Fluorescence (CHCl$_3$): $\lambda$max = 534.5 nm, 575 nm.

EXAMPLE 43

N,N'-Di(12-pentacosyl)perylene-3,4:9,10-tetracarboxylic acid bisimide

Yield = 77° C. UV (CHCl$_3$): $\lambda$max (e) = 458 nm (18150), 489.5 nm, (49480), 526.5 nm (82520).
Fluorescence (CHCl$_3$): = 534.5 nm, 575 nm.
Solid-state fluorescence, pale form: $\lambda$max = 582 nm, 615 nm.
Solid-state fluorescence, dark form: $\lambda$max = 622 nm.

We claim:

1. 3,6-Bis-(2'-methoxyphenyl)-2,5-dihydro-2,5-dimethyl-pyrrole-(3,4-c)pyrrole-1,4-dione of the formula III

* * * * *